United States Patent [19]

Sick

[11] 4,085,322
[45] Apr. 18, 1978

[54] OPTICAL APPARATUS

[75] Inventor: Erwin Sick, Icking, Germany

[73] Assignee: Erwin Sick Gesellschaft mit beschrankter Haftung Optik-Elektronik, Germany

[21] Appl. No.: 705,656

[22] Filed: Jul. 15, 1976

[30] Foreign Application Priority Data

Jul. 21, 1975 Germany .............................. 2532603

[51] Int. Cl.² .............................................. G02B 5/14
[52] U.S. Cl. ...................................... 250/227; 350/299
[58] Field of Search ................ 250/227; 350/286, 287, 350/299

[56] References Cited

U.S. PATENT DOCUMENTS

| | | | |
|---|---|---|---|
| 2,946,253 | 7/1960 | Clark, Jr. ............................. | 250/227 |
| 3,322,032 | 5/1967 | Leach .................................. | 350/299 |
| 3,884,217 | 5/1975 | Wartes ................................ | 350/299 |

*Primary Examiner*—M. Tokar
*Attorney, Agent, or Firm*—Townsend and Townsend

[57] ABSTRACT

Optical apparatus for determining the angle at which light is reflected by a surface being scanned by light spot, wherein in the area of the light beams emanating from the surface is provided a lamellar stepped mirror arrangement which extends in the scanning direction and whose individual planar mirrors are arranged parallel to one another and deflect the light which strikes them to an optical system on whose focal plane is arranged a photo detector array extending at right angles to the optical axis.

A particular application occurs in conjunction with monitoring webs of fabric or paper for surface irregularities faults or errors.

17 Claims, 6 Drawing Figures

OPTICAL APPARATUS

BACKGROUND OF THE INVENTION

The invention relates to an optical apparatus for determining the angle at which light emanates to a surface from a scanning light spot.

It is already known to continuously scan at right angles to the direction of travel by means of a light beam emanating from a laser e.g. webs of fabric or paper which have to be monitored for errors such as surface irregularities. Thus, there is a light spot on the web from which light is reflected in various directions depending on the nature of the surface irregularity. In total, the light emanating from the light spot is reflected in a solid angle whereby the intensity of the light beams in the individual directions is in all characteristic of the surface state. It is already known that the receiving arrangements which monitor the light spot and which generally comprise a light conducting rod (hereinafter sometimes called "light rod") extending parallel to the scanning direction, together with a cylindrical lens positioned in front of the rod, can be arranged at various angles in order to provide the most favourable reception conditions. Generally, the light intensity received by the receiving arrangement is greatest in the direction of the angle of reflection and reduces to a greater or lesser extent at angles diverging therefrom.

The disadvantage of all known receiving arrangements for such scanning light spots is that reception is generally restricted to one or possibly two directions relative to the surface.

BRIEF SUMMARY OF THE INVENTION

The problem of the present invention is to provide a simply constructed, economically manufacturable but operationally reliable optical apparatus for determining the angle at which light from a scanning light spot is reflected by the being monitored. At all times the apparatus must intercept at least a considerable part of the light emanating from the surface at different angles and within this light part must be able to determine angular differences at least in several angular stages.

According to the invention, this problem is solved in that in the area of the light beams emanating from the surface is provided a lamellar stepped mirror arrangement which extends in the scanning direction. The stepped mirror is constructed of individual planar mirrors which are arranged parallel to one another and deflect the light which strikes them to an optical system namely a focusing lens. An array of of photo detectors is positioned in the focal plane of the lens and the array is arranged perpendicular to the optical axis of the lens. The arrangement is preferably such that in the case of a completely satisfactory surface light that is reflected by the monitored surface at a right angle thereto; is combined in the focus of the lens. Light diverging from this normal direction at any angle is also concentrated in the focal plane but at a point which is laterally displaced to a greater or lesser extent from the focus. In the simplest case, the reception screen can comprise a ground glass plate on which appears a light spot distribution characteristic for the surface which can be monitored by simply observing divergencies from a normal distribution.

Preferably, however, the reception screen comprises a plurality of photoelectric or photosensitive cells which are appropriately connected to an evaluating electronic system which transmits an error signal when signals exceeding a specific value appear on receivers located outside the centre. By suitable refinement of the electronic system, it is possible to detect even minor differences in the relative state of the surface being monitored.

Preferably, the light beams emanating at right angles from the surface are deflected by the stepped mirror arrangement 90°.

In the simplest case, the stepped mirror arrangement can be provided on the outside of a light rod which is inclined relative to the surface and the optical axis. The rod can then be arranged, for example, at an angle with a tangent of $1/5$ to $1/10$ to the surface. With a decreasing inclination of the rod it can extend further over the surface in the scanning direction; however the blind areas between the scanned pots becomes larger. For this reason angles with a tangent of $1/10$ should be considered the minimum acceptable.

Relatively narrow blind areas and a very long measuring range are obtained if the stepped mirror arrangement is provided on the side of a light rod facing away from the monitored surface with the rod; positioned parallel to the surface. Due to the total reflections on the walls in a light rod, it can extend over the entire width of the web scanned at right angles to its direction of movement, whereby, however, the intercepted light beams are guided to one or both ends. Since, according to the invention, it is important to have a clearly defined association between light beams striking at a particular angle and the imaging point or points in the focal plane of the optical system, the light rod used must be of optical quality. A reflection angle should be about 60°.

Preferably a prism is provided at each end of the light guide to which the light is reflected and the said prism makes parallel the emerging light beams which pass out at right angles from the surface. This leads to a compact structural arrangement linked with perfect optical conditions.

It is also possible to construct the stepped mirror arrangement in such a way that both sides reflect to opposite ends of the rod. Due to this advantageous further development blind areas between the individual planar mirrors are eliminated so that constant scanning is ensured. However, in this embodiment a receiving optical system with receiving screen must either be provided at both ends or, if provided at one end only, the other end of the rod must be optically mirrored so that light received by it is reflected to said one detector array.

Due to the necessary clearly defined association of light beam and imaging points, the light rod advantageously has a rectangular and preferably a square cross section.

The stepped mirror arrangement is preferably made narrower than the associated rectangular side of the rod, whereby the ratio of the width of the stepped mirror arrangement to the width of the rectangle is advantageously 1 : 5 to 1 : 10. As a result of this construction, the areas of the rectangular light guide located laterally of the stepped mirror arrangement can also be utilised for total reflections.

In order to obtain clearly defined associations, the planar mirrors are all of identical construction and have the same spacing.

Advantageously, a cylindrical lens is arranged between the surface and the stepped mirror arrangement which extends parallel to the surface and which concentrates the light beam emanating from the scanning light spot to the lamellar stepped mirror arrangement.

BRIEF DESCRIPTION OF THE DRAWINGS

Other and further objects of the present invention will be apparent from the description and claims and are illustrated in the accompanying drawings which by way of illustration show preferred embodiments of the invention and the principles thereof, and what are now considered to be the best modes contemplated for applying these principles. Other embodiments of the invention embodying the same or equivalent principles may be used and structural changes may be made if desired by those skilled in the art without departing from the invention and the scope of the appended claims. In the drawings show:

DETAILED DESCRIPTION OF THE PREFERRED EMBODIMENTS

Figure 1:
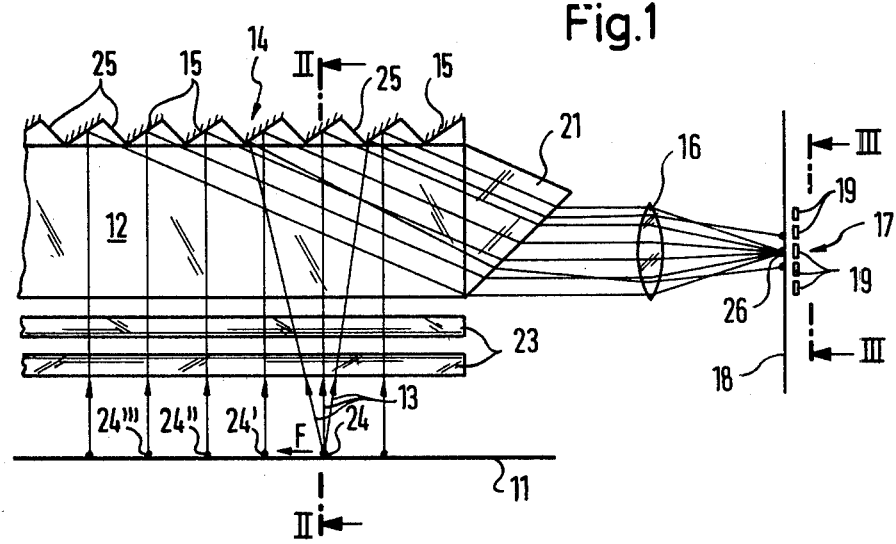
FIG. 1, a shematic side view of an apparatus according to the invention with an only partly shown light guide or pipe.
Figure 2:
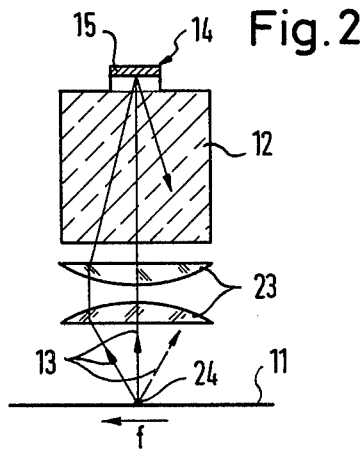
FIG. 2, a schematic section along the line II — II of FIG. 1.
Figure 3:
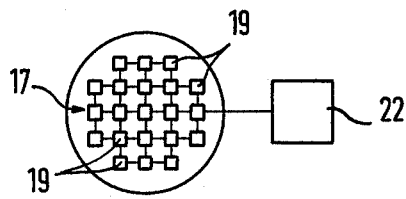
FIG. 3, a schematic view along the line III — III of FIG. 1.

According to FIGS. 1 to 3, the surface 11 of a web of fabric or paper to be monitored moves constantly in the direction of arrow f. A light spot 24 is projected onto the surface in a manner not shown in the drawing, e.g. by means of a laser and a suitable optical system. The light spot is scanned in the direction of the arrow F in FIG. 1, across the monitored web so that it successively occupies positions 24', 24", 24"'etc. until the scanning cycle recommences again. A mirror wheel is generally used for scanning purposes.

Figure 1A:
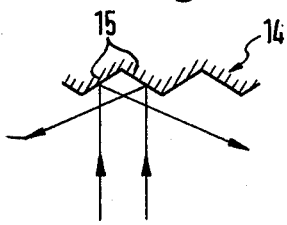
FIG. 1a, a special stepped mirror arrangement in which both sides are utilised for reflections so that the monitoring of the scanning light spot without blind areas is ensured.

Above surface 11 and parallel to it and to the scanning direction F is arranged a cylindrical lens. A light rod or pipe 12 which, according to FIG. 2, has a rectangular cross-section is positioned above the cylindrical lens. At the top and in the centre of light rod 12 is mounted, e.g. bonded, a stepped mirror arrangement 14 which comprises planar mirrors 15 and adaptors 25 which in the embodiment of FIG. 1 can be non-reflecting, whereas in the embodiment of FIG. 1a, oppositely inclined planar mirrors 15 are positioned directly behind one another.

The inclination of planar mirror 15 is such that the beams passing from the surface 11 at right angles are reflected downwards at an angle, as shown in FIG. 1, to a prism 21 arranged on the end and the said prism directs the light beams which have emanated at right angles from surface 11 parallel to the rod axis. A lens 16 located in the path of the beam combines the beams in its focal plane 18.

As shown in FIG. 1, lens 16 also combines in focal plane 18 at points located adjacent focal points 26 those light beams 13 which do not emanate from surface 11 at right angles. For example, two beams which emanate from spot 24 not at right angles to the surface 11 are shown, one meets the focal plane 18 above and the other below focus 26.

As a result of the cylindrical lens 23 in FIG. 2, the light emanating from spot 24 is concentrated on the stepped mirror arrangement 14. The light beams 13 emanating from spot 24 at different angles also strike the stepped mirror arrangement 14 at different angles in the cross-sectional plane of light rod 12, so that they are not reflected within the vertical median longitudinal plane of the light rod 12 but instead are, for example, reflected as shown in FIG. 2. The light beam indicated by dotted lines in FIG. 2 would be reflected in precisely the opposite manner to the stepped mirror arrangement 14. As a result of these conditions, in the cross-sectional plane of FIG. 2 light beams not emanating at right angles on the surface 11 are concentrated in the focal plane 18 laterally and in the vicinity of focus 26.

By superimposing the effects shown in FIGS. 1 and 2, the light beams concentrated on focal plane 18 can be located at other points surrounding focus 26.

If in accordance with FIGS. 1 and 3 an X-Y array of multiple photoelectric cells 19 is, for example, mounted in focal plane 18. The electrical signals generated by the individual photoelectric cells are a measure for the intensity of the light emanating from surface 11 at a particular angle. Thus, together photoelectric cells 19 form a detector array 17 by means of which the light intensities in the various angular ranges can be determined. The finer the array 17 the smaller the angular differences which can be determined. However, it is generally sufficient if only a few photoelectric cells 19 are provided around the central cell arranged in focus 26. This in itself constitutes considerable advantage compared with the known receiving devices which normally can only determine and measure the light emanating from the monitored web surface at a specific angle.

By passing the electrical signals transmitted by the individual photoelectric cells 19 to an evaluating electronic system 22, any desired evaluation of the signals received can be performed. In the simplest case, the photoelectric cells 19 are connected in such a way that on determining particular divergencies, i.e. signals exceeding a predetermined value, an error signal is transmitted by photoelectric cells located adjacent to focus 26.

Figure 4:
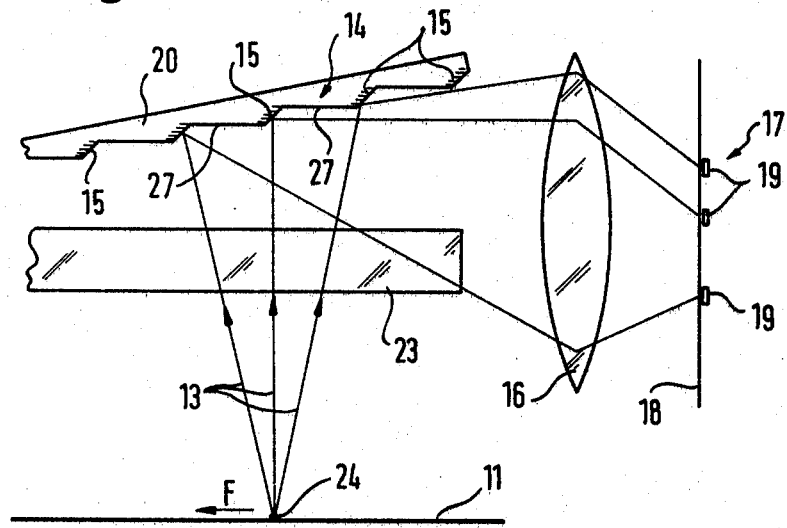
FIG. 4, a schematic side view of a simplified construction of the apparatus according to the invention.

FIG. 4 shows a simplified embodiment, wherein following the cylindrical lens 23 a light rod 20 inclined relative to the surface 11 is provided which on its bottom, e.g. the rod sidefacing the monitored web surface carries a stepped mirror arrangement 14. The planar mirrors 15 reflect the light beams emanating from light spot 24 to an optical system 16 which deflects the light beams to different points on its focal plane 18, depending on the emergence angle from the surface 11. Further photoelectric cells 19 are provided on the individual spots of the detector array 17. The plan view of the receiving screen is identical to FIG. 3.

The greater the inclination of the rod, the smaller the blind areas 27 between planar mirrors 15. In the limiting case of arranging rod 20' at 45° to the surface 11, only a single planar mirror could be provided, but the scanning length would be restricted.

Figure 1B:
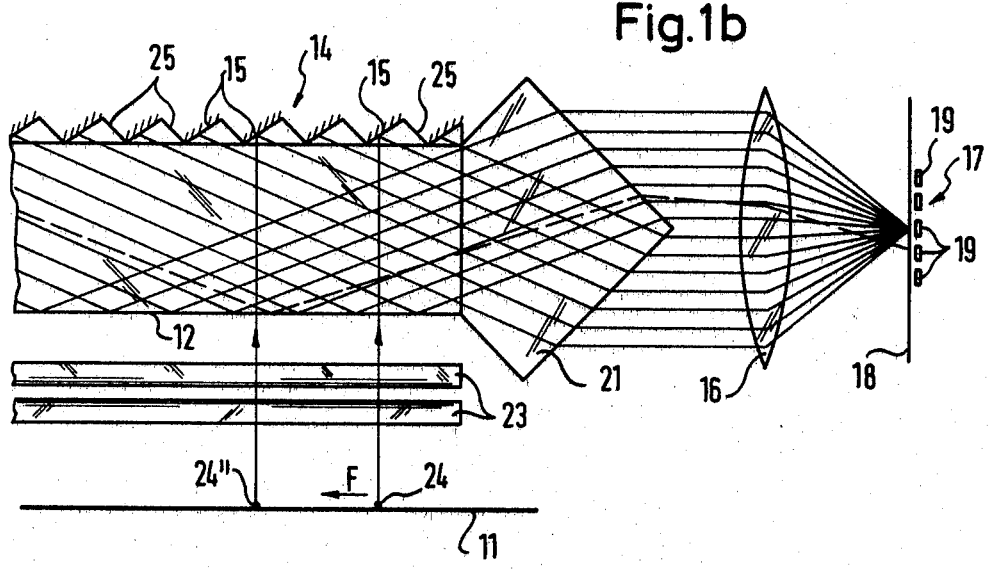
FIG. 1b, a variant of FIG. 1.

FIG. 1b shows a view analogous to FIG. 1, whereby through the special symmetrical construction of the prism it is ensured that even beams which are totally reflected by the walls of rod 12 reach the focal plane 18. The beam shown in dotted lines as an example of a beam diverging from the normal direction is intended to show that the same rules as indicated for direct beams in FIG. 1 also apply to the totally reflected beams, i.e. when the beams emanating from the web 11 diverge from a normal direction, the image point in the focal plane 18 of focus 26 is off set to one side or the other depending on the direction of the divergence. It is also possible to permit the beams to emerge from guide 12 at an angle to the guide axis, in which case two arrangements comprising a lens 16 and photoelectric cells 19 must be provided at the rod end in the path of the outgoing beams.

The invention is not limited to the embodiments described and represented hereinbefore, and various modifications can be made thereto without passing beyond the scope of the invention.

What is claimed is:

1. Apparatus for determining the angle at which light from a light spot linearly scanning a monitored surface is reflected by the surface, the apparatus comprising: a light conducting rod having a substantially rectangular cross-section, extending in the direction of the light spot scanning direction, and positioned so that light from the spot reflected by the surface strikes the rod; a plurality of serially arranged mirrors extending in the scanning direction and having like angular inclination relative to the surface, the mirrors being positioned to receive and reflect light from the spot striking the rod; an optical system including focusing lens means positioned to receive light reflected by the mirrors and imaging such light in a focal plane of the lens means; and light detecting means disposed in said focal plane and surrounding a focal point of the lens means for detecting such imaged light and for determining the position of such imaged light relative to said focal point, whereby an angular divergence of light from the spot reflected by the surface due to surface irregularities results in corresponding offsets of the imaged light relative to said focal point for the detection of such irregularities.

2. Appartus according to claim 1 wherein one of the photo detectors is disposed in said focal point, and including a plurality of additional photo detectors laterally offset from said one detector and also disposed in said focal plane.

3. Apparatus according to claim 1 wherein the rod has a square cross-section.

4. Apparatus for monitoring a web for surface irregularities by linearly scanning a light spot over the web surface, the apparatus comprising a plurality of serially arranged, parallel mirrors which are angularly inclined relative to the surface and which extend along the scanning line of the spot; means for directing light from the spot reflected by the surface onto the mirrors; lens means positioned for receiving light reflected by the mirrors and for on a focal plane of the lens means disposed perpendicular to an axis of the rod; an array of light detectors arranged about the focal point of the lens means for detecting light imaged by the lens means lateral of its focal point; and means for generating an error signal if light of a predetermined intensity strikes the light detector array lateral of the focal point of the lens means; whereby deviations in the angularity of light from the spot reflected by the surface due to surface irregularities cause corresponding lateral offsets of the imaged light relative to the focal point and indicates the presence of such a surface irregularity.

5. An apparatus according to claim 1, wherein the light detecting means comprises a plurality of photoelectric cells.

6. An apparatus according to claim 1, wherein light reflected by the surface substantially perpendicular to the surface is deflected by the mirrors at an angle of about 60°.

7. An apparatus according to claim 1, wherein the mirrors are provided on an outside of the light transmitting rod and the rod is inclined relative to the surface and the optical axis of the lens means.

8. An apparatus according to claim 1, wherein the mirrors are disposed on a side of the rod facing away from the surface, the rod being further positioned parallel to the surface.

9. An apparatus according to claim 8, including a prism mounted to at least one end of the rod to which the mirrors reflect the light, the prism being formed and positioned so that the light reflected by the surface at a right angle thereto emerges from the prism substantially parallel to the surface and to an axis of the rod.

10. An apparatus according to claim 8, including another plurality of serially arranged mirrors positioned to receive light from the spot striking the rod and to reflect such light in a direction opposite to that in which the first mentioned mirrors reflect light striking them.

11. An apparatus according to claim 5, wherein the mirrors have a lesser width than the associated side of the rod.

12. An apparatus according to claim 5, wherein the mirrors are narrower than the rod side by a ratio of 1:5 to 1:10.

13. An apparatus according to claim 1, wherein the mirrors are identical planar mirrors having an equal spacing.

14. An apparatus according to claim 5, including an evaluating electronic system connected with the photoelectric cells for generating an error signal when light of a given intensity strikes cells located outside the focal point of the lens means.

15. An apparatus according to claim 1, including a cylindrical lens between the surface and the mirrors.

16. An apparatus according to claim 8, wherein the mirrors are inclined relative to the axis of the rod so that light reflected from the surface is reflected by the mirrors into the rod at total reflection angles with respect to the rod.

17. An apparatus according to claim 13, wherein the cylindrical lens is formed so that all light from the spot reflected by the surface and striking the cylindrical lens is concentrated on the mirrors.

* * * * *